US00PP19104P2

(12) United States Plant Patent
Smith

(10) Patent No.: US PP19,104 P2
(45) Date of Patent: Aug. 19, 2008

(54) ***ASTER* PLANT NAMED 'YOFROLIC'**

(50) Latin Name: *Aster hybrida*
Varietal Denomination: Yofrolic

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/705,874

(22) Filed: Feb. 14, 2007

(51) Int. Cl.
*A01H 6/00* (2006.01)

(52) U.S. Cl. ..... Plt./355

(58) Field of Classification Search ..... Plt./355
See application file for complete search history.

*Primary Examiner*—Kent Bell
(74) *Attorney, Agent, or Firm*—C. A. Whealy

(57) ABSTRACT

A new and distinct cultivar of *Aster* plant named 'Yofrolic', characterized by its uniform, upright and mounded plant habit; freely branching growth habit; dark green-colored foliage; uniform and freely flowering habit; natural flowering season later August in the northern hemisphere; daisy-type inflorescences with violet-colored ray florets; and good garden performance.

1 Drawing Sheet

Botanical designation: *Aster hybrida.*
Cultivar denomination: 'Yofrolic'.

BACKGROUND OF THE INVENTION

The present invention relates to a new and distinct cultivar of *Aster* plant, botanically known as *Aster hybrida* and hereinafter referred to by the name 'Yofrolic'.

The objective of the breeding program is to create new potted *Aster* cultivars with uniform and rounded plant growth habit, good vigor and strong branching habit, numerous inflorescences, desirable and unique floret colors, and good garden performance.

The new *Aster* originated from an open-pollination in February, 2001, in Alva, Fla. of an unnamed *Aster hybrida* seedling selection, not patented, as the female, or seed, parent with an unknown *Aster hybrida* seedling selection, as the male, or pollen, parent. The new *Aster* was discovered and selected by the Inventor as a single flowering plant within the progeny of the stated open-pollination in a controlled environment Alva, Fla. in October, 2002. The selection of this plant was based on its uniform plant growth habit, vigor and desirable ray floret color.

Asexual reproduction of the new *Aster* by vegetative tip cuttings was first conducted in Alva, Fla. in December, 2002. Asexual reproduction by cuttings has shown that the unique features of this new *Aster* are stable and reproduced true to type in successive generations.

SUMMARY OF THE INVENTION

Plants of the cultivar Yofrolic have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yofrolic'. These characteristics in combination distinguish 'Yofrolic' as a new and distinct potted *Aster* cultivar.

1. Uniform, upright and mounded plant habit.
2. Freely branching growth habit.
3. Dark green-colored foliage.
4. Uniform and freely flowering habit.
5. Natural flowering season late August in the northern hemisphere.
6. Daisy-type inflorescences with violet-colored ray florets.
7. Good garden performance.

Plants of the new *Aster* differ from plants of the female parent selection in the following characteristics:

1. Plants of the new *Aster* are larger and more mounding than plants of the female parent selection.
2. Plants of the new *Aster* flower about one week earlier than plants of the female parent selection when grown under natural season conditions.
3. Ray florets of plants of the new *Aster* do not fade as quickly as ray florets of plants of the female parent selection.

Plants of the new *Aster* can be compared to plants of the *Aster* cultivar Patricia Ballard, not patented. In side-by-side comparisons conducted in Alva, Fla., plants of the new *Aster* differed from plants of the cultivar Patricia Ballard in the following characteristics:

1. Plants of the new *Aster* were smaller and more mounding than plants of the cultivar Patricia Ballard.
2. Plants of the new *Aster* were stronger than plants of the cultivar Patricia Ballard.
3. Plants of the new *Aster* flowered a few days earlier than plants of the cultivar Patricia Ballard when grown under natural season conditions.
4. Plants of the new *Aster* and the cultivar Patricia Ballard differed in ray floret coloration.
5. Inflorescences of plants of the new *Aster* lasted longer than inflorescences of plants of the cultivar Patricia Ballard.

Plants of the new *Aster* can be compared to plants of the *Aster* cultivar Thyra Viking, disclosed in U.S. Plant Pat. No.

10,361. In side-by-side comparisons conducted in Alva, Fla., plants of the new *Aster* differed from plants of the cultivar Thyra Viking in the following characteristics:

1. Plants of the new *Aster* were smaller and more uniform than plants of the cultivar Thyra Viking.
2. Plants of the new *Aster* flowered earlier than plants of the cultivar Thyra Viking when grown under natural season conditions.
3. Plants of the new *Aster* and the cultivar Thyra Viking differed in ray floret coloration.

BRIEF DESCRIPTION OF THE PHOTOGRAPHS

The accompanying photographs illustrate the overall appearance of the new *Aster*. These photographs show the colors as true as it is reasonably possible to obtain in colored reproductions of this type. Colors in the photographs may differ slightly from the color values cited in the detailed botanical description which accurately describe the colors of the new *Aster*.

The photograph at the bottom of the sheet comprises a side perspective view of a typical flowering plant of 'Yofrolic'.

The photograph at the top of the sheet is a close-up view of typical inflorescences of 'Yofrolic'.

DETAILED BOTANICAL DESCRIPTION

The aforementioned photographs and following observations and measurements describe plants grown during the summer in Pendleton, S.C. in an outdoor nursery and under conditions and practices which approximate those generally used in commercial potted *Aster* production. During the production of the plants, day temperatures averaged 32° C. and night temperatures averaged 21° C. Rooted cuttings were planted in 20 cm-containers, exposed to natural season conditions. Plants used in the photographs and for the description were about three months old. In the following description, color references are made to The Royal Horticultural Society Colour Chart, 1995 Edition, except where general terms of ordinary dictionary significance are used.

Botanical classification: *Aster hybrida* cultivar Yofrolic.

Parentage:

*Female, or seed, parent.*—Unnamed *Aster hybrida* seedling selection, not patented.

*Male, or pollen, parent.*—Unknown *Aster hybrida* seedling selection, not patented.

Propagation:

*Type.*—Terminal vegetative cuttings.

*Time to initiate roots.*—About ten days at temperatures of about 22° C.

*Time to produce a rooted young plant.*—About 16 to 18 days at temperatures of about 22° C.

*Root description.*—Fine, fibrous; white in color.

*Rooting habit.*—Freely branching.

Plant description:

*Appearance.*—Herbaceous daisy-type potted *Aster*. Upright with lateral branches somewhat outwardly spreading; inverted triangle with uniformly mounded crown. Strong and freely branching growth habit with about ten primary lateral branches each with numerous secondary and tertiary branches; dense and full plants. Vigorous growth habit.

*Plant height.*—About 21 cm.

*Plant width.*—About 30 cm.

*Lateral branches.*—Length: About 19 cm. Diameter: About 3 mm. Internode length: About 1.4 cm. Strength: Strong. Texture: Smooth, glabrous. Color: Close to 146A.

Foliage description:

*Arrangement.*—Alternate, simple; sessile.

*Length.*—About 3 cm.

*Width.*—About 5 mm.

*Shape.*—Lanceolate.

*Apex.*—Acute.

*Base.*—Clasping.

*Margin.*—Entire.

*Texture, upper and lower surfaces.*—Smooth, glabrous.

*Color.*—Developing foliage, upper and lower surfaces: Close to 147A. Fully expanded foliage, upper surface: Close to 147A; venation, 147B. Fully expanded foliage, lower surface: Close to 147B; venation, 147B.

Inflorescence description:

*Appearance.*—Daisy-type inflorescence form with ligulate-shaped ray florets. Inflorescences borne on terminals above and beyond the foliage. Disk and ray florets arranged acropetally on a capitulum. Inflorescence not fragrant.

*Flowering response.*—Under natural conditions, plants flower in late August in the Northern Hemisphere. Inflorescences persistent. Inflorescences last about four weeks on the plant.

*Quantity of inflorescences.*—Freely flowering, about 58 inflorescences develop per lateral stem.

*Inflorescence bud.*—Height: About 1.1 cm. Diameter: About 8 mm. Shape: Ovoid. Color: Close to 75C.

*Inflorescence size.*—Diameter: About 3 cm. Depth (height): About 1.5 cm. Diameter of disc: About 1 cm. Receptacle height: About 7 mm. Receptacle diameter: About 1.4 cm.

*Ray florets.*—Length: About 1.7 cm. Width: About 2.5 mm. Shape: Ligulate. Apex: Slightly emarginate. Base: Acute to attenuate. Margin: Entire. Texture, upper and lower surfaces: Smooth, glabrous, satiny. Orientation: Initially upright, then about 90° from vertical or perpendicular to peduncle; apices reflexing with development. Number of ray florets per inflorescence: About 92 arranged in about six or seven whorls. Color: When opening, upper surface: Close to 88B to 88C. When opening, lower surface: Close to 77D. Fully opened, upper surface: Close to 87A; color becoming closer to 76A with development. Fully opened, lower surface: Close to 77D; color becoming closer to 76C to 76D with development.

*Disc florets.*—Arrangement: Massed at center of receptacle. Shape: Tubular, elongated. Apex: Five-pointed. Length: About 1.2 cm. Width: About 2 mm. Number of disc florets per inflorescence: About 60. Color, immature: Apex: Close to 150B. Mid-section: Close to 150D. Base: Close to 157A. Color, mature: Apex: Close to 156B. Mid-section: Close to 156B. Base: Close to 157A.

*Phyllaries.*—Number of phyllaries per inflorescence: About 60 arranged in about eight whorls. Length: About 5 mm. Width: About 1 mm. Shape: Lanceolate. Apex: Acute. Base: Truncate. Texture, upper and lower surfaces: Smooth, glabrous. Color, upper and lower surfaces: Close to 147A.

*Peduncles.*—Length: First peduncle: About 4.3 cm. Fourth peduncle: About 6.5 cm. Diameter (first peduncle): About 1.5 mm. Angle: Upright to about 45' to 50° from vertical. Strength: Strong, flexible. Texture: Smooth, glabrous; longitudinally ridged. Color: Close to 147A.

*Reproductive organs.*—Androecium: Present on disc florets only. Filament length: About 4 mm. Filament color: Close to 1C. Anther shape: Slender, elongated oblong. Anther length: About 2 mm. Anther color: Close to 2C. Pollen amount: Scarce. Pollen color: Close to 2C. Gynoecium: Present on both ray and disc florets. Pistil length: About 6 mm. Stigma shape: Bi-parted. Stigma color: Close to 157A. Style length: About 4 mm. Style color: Close to 157C. Ovary color: Close to 157A.

*Seed/fruit.*—Seed and fruit production has not been observed.

Disease/pest resistance: Resistance to pathogens and pests common to *Asters* has not been observed on plants grown under commercial conditions.

Garden performance: Plants of the new *Aster* have been observed to be rain and wind tolerant and to tolerate temperatures from 2° C. to about 38° C.

It is claimed:

1. A new and distinct *Aster* plant named 'Yofrolic' as illustrated and described.

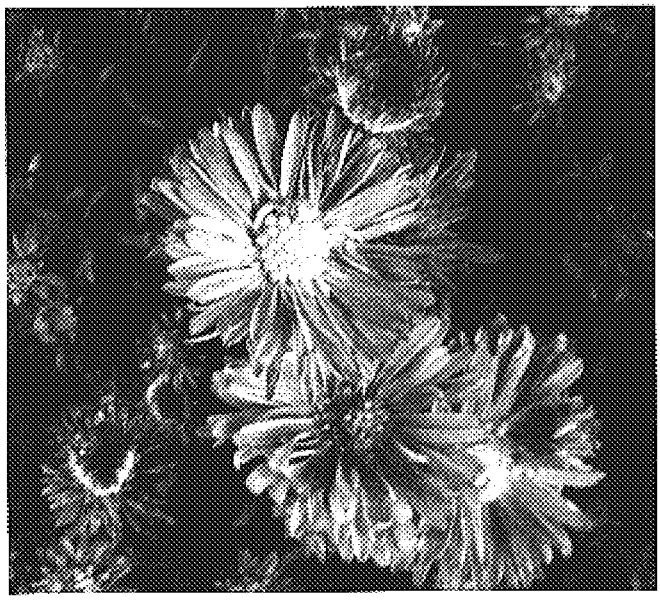
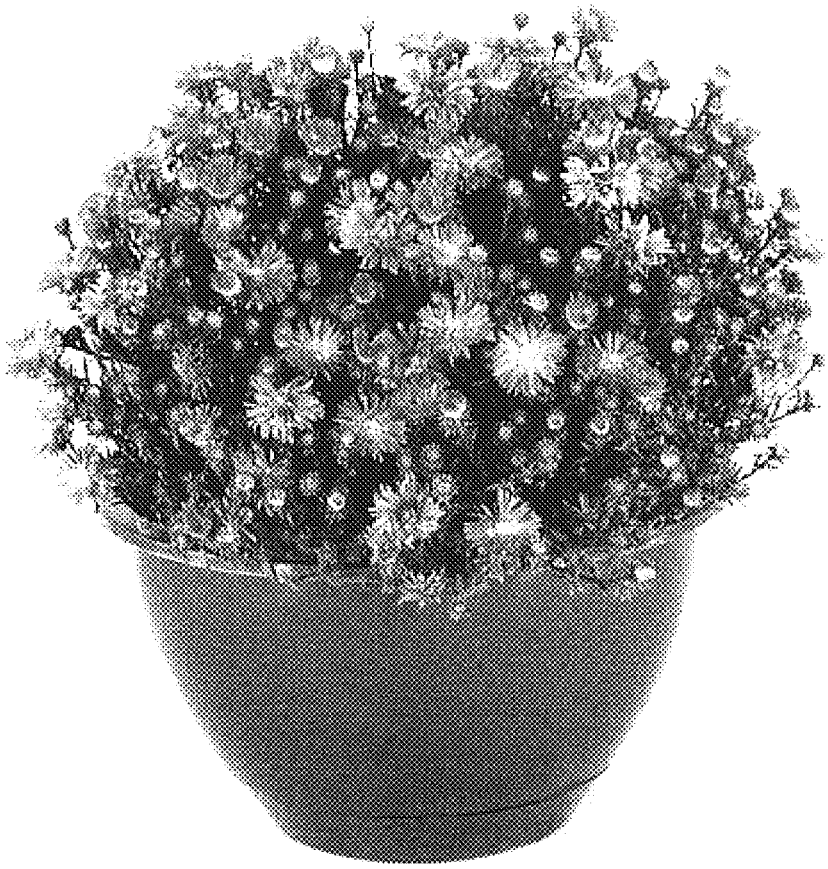

* * * * *